United States Patent
Strauss

(10) Patent No.: US 9,345,499 B2
(45) Date of Patent: May 24, 2016

(54) PRESSURE ACTIVATED FOREIGN BODY REMOVAL SYSTEM AND METHOD OF USE

(75) Inventor: Brian Michael Strauss, Trabuco Canyon, CA (US)

(73) Assignee: Covidien LP, Mansfield, MA (US)

( * ) Notice: Subject to any disclaimer, the term of this patent is extended or adjusted under 35 U.S.C. 154(b) by 849 days.

(21) Appl. No.: 13/481,813

(22) Filed: May 26, 2012

(65) Prior Publication Data

US 2013/0102996 A1   Apr. 25, 2013

Related U.S. Application Data

(60) Provisional application No. 61/490,280, filed on May 26, 2011.

(51) Int. Cl.
*A61B 17/22* (2006.01)
*A61B 17/221* (2006.01)
*A61M 25/10* (2013.01)

(52) U.S. Cl.
CPC ......... *A61B 17/22032* (2013.01); *A61B 17/221* (2013.01); *A61B 2017/2212* (2013.01); *A61M 2025/109* (2013.01)

(58) Field of Classification Search
CPC .................. A61B 17/22032; A61M 25/1009; A61M 25/104; A61M 2025/1052; A61M 2025/1068; A61M 2025/109
See application file for complete search history.

(56) References Cited

U.S. PATENT DOCUMENTS

| | | |
|---|---|---|
| 3,831,587 A | 8/1974 | Boyd |
| 3,896,815 A | 7/1975 | Fettel et al. |
| 4,611,594 A | 9/1986 | Grayhack et al. |
| 5,011,488 A | 4/1991 | Ginsburg |
| 5,102,415 A | 4/1992 | Guenther et al. |
| 5,308,356 A | 5/1994 | Blackshear, Jr. et al. |
| 5,549,626 A | 8/1996 | Miller et al. |
| 5,713,853 A | 2/1998 | Clark et al. |
| 5,868,753 A | 2/1999 | Schatz |
| 5,908,435 A | 6/1999 | Samuels |
| 5,971,938 A | 10/1999 | Hart et al. |
| 6,139,517 A | 10/2000 | Macoviak et al. |
| 6,277,136 B1 | 8/2001 | Bonutti |
| 6,626,861 B1 * | 9/2003 | Hart et al. .................. 604/96.01 |
| 6,682,505 B2 | 1/2004 | Bates et al. |
| 6,682,543 B2 | 1/2004 | Barbut et al. |
| 6,702,830 B1 | 3/2004 | Demarais et al. |
| 7,300,429 B2 | 11/2007 | Fitzgerald et al. |
| 7,837,702 B2 | 11/2010 | Bates |
| 7,846,175 B2 | 12/2010 | Bonnette et al. |
| 8,784,441 B2 | 7/2014 | Rosenbluth et al. |
| 2001/0037126 A1 | 11/2001 | Stack et al. |
| 2003/0163158 A1 | 8/2003 | White |
| 2005/0085826 A1 | 4/2005 | Nair et al. |

(Continued)

FOREIGN PATENT DOCUMENTS

| | | |
|---|---|---|
| EP | 2158858 A1 | 3/2010 |
| WO | WO-84/01513 A1 | 4/1984 |

(Continued)

*Primary Examiner* — Kami A Bosworth

(74) *Attorney, Agent, or Firm* — Mark J. Kertz, Esq.

(57) ABSTRACT

A catheter is provided for retrieving an embolus or foreign body from a body lumen. The catheter can have a distal segment which is movable from a reduced outside diameter for positioning at a target site. Further, the catheter can have an enlarged outside diameter suitable for thrombectomy or foreign body retrieval.

20 Claims, 5 Drawing Sheets

(56) References Cited

U.S. PATENT DOCUMENTS

| | | |
|---|---|---|
| 2005/0159770 A1 | 7/2005 | Divani et al. |
| 2005/0187570 A1 | 8/2005 | Nguyen et al. |
| 2006/0135962 A1 | 6/2006 | Kick et al. |
| 2006/0282116 A1 | 12/2006 | Lowe et al. |
| 2007/0027520 A1 | 2/2007 | Sherburne |
| 2008/0058836 A1 | 3/2008 | Moll et al. |
| 2009/0043330 A1 | 2/2009 | To |
| 2009/0054918 A1 | 2/2009 | Henson |
| 2010/0191272 A1 | 7/2010 | Keating |
| 2010/0211156 A1 | 8/2010 | Linder et al. |
| 2011/0077680 A1 | 3/2011 | Heuser |
| 2011/0160762 A1 | 6/2011 | Hogendijk et al. |
| 2011/0213290 A1 | 9/2011 | Chin et al. |
| 2011/0218560 A1 | 9/2011 | Ramzipoor et al. |
| 2011/0288529 A1 | 11/2011 | Fulton |

FOREIGN PATENT DOCUMENTS

| | | |
|---|---|---|
| WO | WO-92/18195 A1 | 10/1992 |
| WO | WO-2008/021013 A1 | 2/2008 |
| WO | WO-2009/120761 A1 | 10/2009 |
| WO | WO-2010/001405 A1 | 1/2010 |
| WO | WO-2012/009675 | 1/2012 |

\* cited by examiner

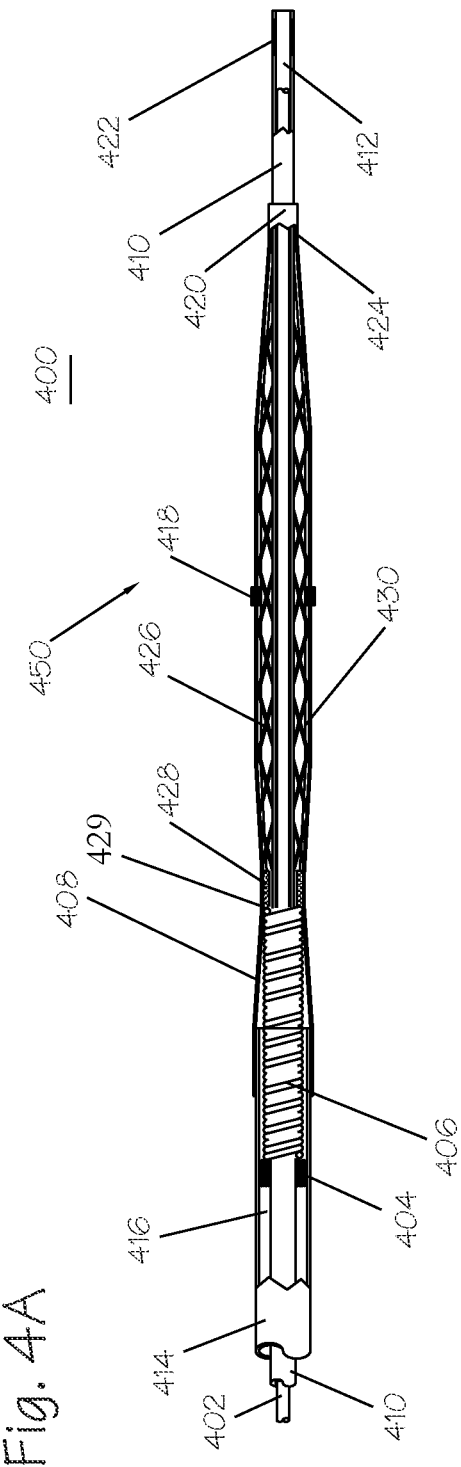
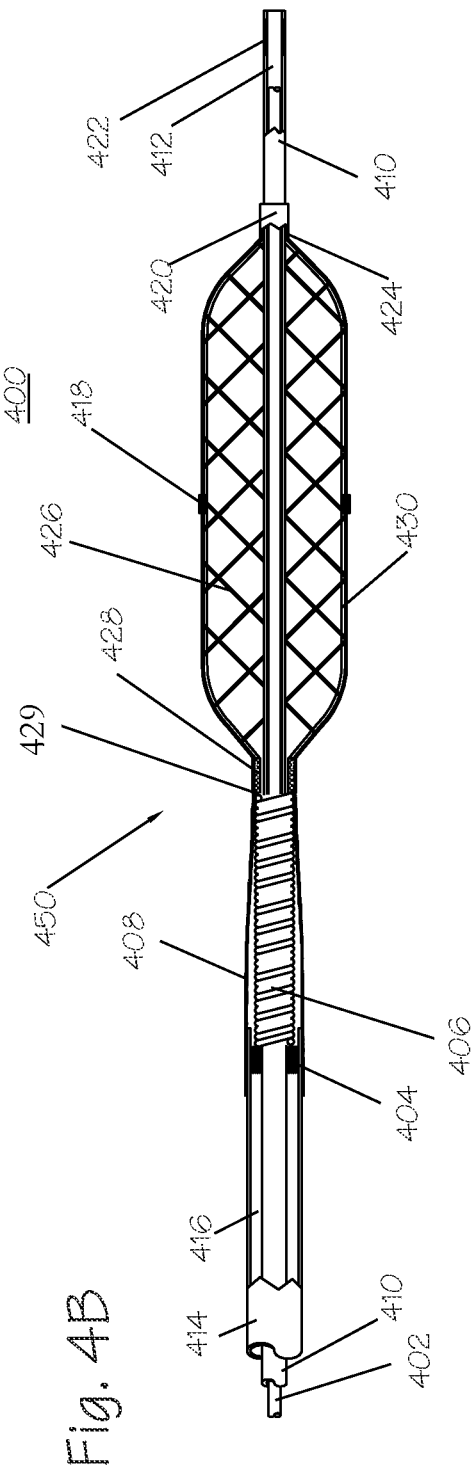
Fig. 4A
Fig. 4B

PRESSURE ACTIVATED FOREIGN BODY REMOVAL SYSTEM AND METHOD OF USE

This application claims priority to U.S. Provisional Application 61/490,280 filed May 26, 2011.

FIELD OF THE INVENTION

The inventions described below relate the field of medical devices for percutaneously accessing and performing therapy on body lumens and cavities, and more particularly, to methods and devices for clot or debris removal within the cardiovascular system

BACKGROUND OF THE INVENTION

Stroke is the third most common cause of death in the United States and the most disabling neurologic disorder. Approximately 700,000 patients suffer from stroke annually. Stroke is a syndrome characterized by the acute onset of a neurological deficit that persists for at least 24 hours, reflecting focal involvement of the central nervous system, and is the result of a disturbance of the cerebral circulation. Its incidence increases with age. Risk factors for stroke include systolic or diastolic hypertension, hypercholesterolemia, cigarette smoking, heavy alcohol consumption, and oral contraceptive use.

Eighty percent strokes are ischemic strokes and are caused by occluded vessels that deprive the brain of oxygen-carrying blood (the remaining 20% of strokes are hemorrhagic strokes, which result in bleeding into the brain). Ischemic strokes are often caused by emboli or pieces of thrombotic tissue that have dislodged from other body sites or from the cerebral vessels themselves to occlude in the narrow cerebral arteries more distally. When a patient presents with neurological symptoms and signs, which resolve completely within 1 hour, the term transient ischemic attack (TIA) is used. Etiologically, TIA and ischemic stroke share the same pathophysiologic mechanisms and thus represent a continuum based on persistence of symptoms and extent of ischemic insult.

Emboli occasionally form around the valves of the heart or in the left atrial appendage during periods of irregular heart rhythm and then are dislodged and follow the blood flow into the distal regions of the body. Those emboli can pass to the brain and cause an embolic stroke. Many such occlusions occur in the middle cerebral artery (MCA), although such is not the only site where emboli come to rest.

Ischemic stroke is sometimes treated by injecting tissue plasminogen activator (t-PA) or Activase® into the patient's blood stream. However, treatment with systemic t-PA is associated with increased risk of intracerebral hemorrhage and other hemorrhagic complications. Patients treated with t-PA are more likely to sustain a symptomatic intracerebral hemorrhage during the first 36 hours of treatment. The frequency of symptomatic hemorrhage increases when t-PA is administered beyond 3 hours from the onset of a stroke. Besides the time constraint in using t-PA in acute ischemic stroke, other contraindications include the following: if the patient has had a previous stroke or serious head trauma in the preceding 3 months, if the patient has a systolic blood pressure above 185 mmHg or diastolic blood pressure above 110 mmHg, if the patient requires aggressive treatment to reduce the blood pressure to the specified limits, if the patient is taking anticoagulants or has a propensity to hemorrhage, and/or if the patient has had a recent invasive surgical procedure. Therefore, only a small percentage of selected stroke patients are qualified to receive t-PA.

Stroke is sometimes treated by attempting to re-establish blood flow in the blocked artery. Certain percutaneous methods have been utilized for reestablishing blood flow. A common percutaneous technique is referred to as balloon angioplasty where a balloon-tipped catheter is introduced to a blood vessel, advanced to the point of the occlusion and inflated in order to dilate the stenosis. Balloon angioplasty is appropriate for treating vessel stenosis but is not effective for treating acute thromboemboli. In patients with vertebral artery occlusions, treatment with angioplasty often results in disastrous complications due to embolization of the occlusive lesion downstream to the basilar artery. Emboli small enough to pass through the vertebral arteries into the larger basilar artery are usually arrested at the top of the basilar artery, where it bifurcates into the posterior cerebral arteries. The resulting reduction in blood flow to the ascending reticular formation of the midbrain and thalamus produces immediate loss of consciousness.

Another percutaneous technique is to place a microcatheter near the clot and infuse streptokinase, urokinase or other thrombolytic agents to dissolve the clot. Unfortunately, thrombolysis typically takes hours to days to be successful. Additionally, thrombolytic agents can cause severe hemorrhage and in many patients the agents cannot be used at all.

Another percutaneous technique is to place a guide catheter proximate the clot and aspirate the clot into the guide catheter. This procedure requires that the guide catheter be brought into close proximity of the clot in order to be effective. Proper placement may be difficult or impossible. Furthermore, a highly aggregated, cohesive clot may not easily be aspirated into a guide catheter without prior thrombolysis or breakdown into small pieces.

Yet another percutaneous technique is to place an expandable structure, located at or near the distal end of a catheter, through a vessel obstruction and expand that structure. The expandable structure can be used to pull the clot back into a guide catheter with its open end placed nearby. Activation of the expandable structure, however, using linkages or other mechanisms can be difficult to perform or control due to the high amount of friction present in a long cerebrovascular catheter with extremely small lumens.

Another problematic area is the removal of foreign bodies. Foreign bodies introduced into the circulation can be fragments of catheters, pacemaker electrodes, guide wires, and erroneously placed embolic material such as thrombogenic coils. The use of such removal devices is difficult and sometimes unsuccessful.

Thus, there exists a need for the development of a device that can be percutaneously introduced, endovascularly advanced to the target lesion, moved across or into the obstruction, and deployed in a controlled, reliable manner into the circulatory system for the removal of viscoelastic clots and foreign bodies without the risk of clot disgorgement, flaking, or incomplete removal. The system needs to, then, be retracted, along with the obstruction from the target vessel. There is also a need for a device, which could be used as a temporary arterial or venous filter to capture and remove thromboemboli formed during endovascular procedures.

SUMMARY OF THE INVENTIONS

The present inventions are directed to methods and devices for removing obstructions from blood vessels. The devices may be used to retrieve and remove clots and other biological obstructions. The device may also be used to retrieve embolic coils and the like which have been misplaced or have migrated to an undesirable location.

The laterally, radially, diametrically, or circumferentially expandable structure (hereinafter "expandable structure") can be employed to secure the distal end of the therapeutic catheter to a specific location within a vessel. The expandable structure can also be used to generate a screen or net capable of preventing emboli from passing while still allowing for blood flow. The expandable structure can be used as a temporary stent to expand a stenosis within a vessel. The expandable structure can be used to create a temporary occlusion to a vessel. The expandable structure can be used as a flow modifier for an aneurysm or as a neck bridge. The expandable structure can be used as a localization device to temporarily secure another device in place within a vessel. The expandable structure can be used as a delivery system for thrombolytics, embolic materials, or implants.

The proximal end of the expandable structure can be affixed or integrally formed to a ring, tube, C-collar, or sleeve, which slidably moves forward or backward along the axis of the guide catheter. The expandable structure can comprise a mesh coupled to ring structures at the first end and the second end of the expandable structure. Further, the expandable structure can comprise a plurality of longitudinal struts that are connected to ring structures at the first end and the second end of the expandable structure.

The ring can be advanced distally, or moved proximally, by means of a linkage slidably disposed through one or more lumens in the catheter shaft and actuated at the proximal end of the catheter. The distal end of the linkage, which can be a wire, rod, tube, or other axially elongate structure, can be affixed to the ring and cause the ring to move proximally, distally, or both. A spring can be used to move the ring proximally or distally. For example, if the linkage is a polymer thread, having little column strength, the spring can cause the ring to move distally while the linkage can cause the ring to move proximally. The linkage can support tension but not compression. Some rods can support column strength and compression and, thus, can force the ring distally.

The ring can be affixed to a fluidic system that can be pressurized to move, or force, the ring forward toward the distal tip, or depressurized to create a vacuum, or remove incompressible fluid, and move the ring backward, away from the distal tip of the catheter.

BRIEF DESCRIPTION OF THE DRAWINGS

FIG. 4A illustrates a side partial breakaway view of a therapeutic catheter in its first, unexpanded configuration, wherein an annular piston is affixed to the proximal end of the expandable element.

FIG. 4B illustrates a side partial breakaway view of the therapeutic catheter of FIG. 4A in its second, expanded configuration, wherein the annular piston has advanced distally, moving the proximal end of the expandable structure distally to reduce its length and increase its diameter.

DETAILED DESCRIPTION OF THE PREFERRED EMBODIMENTS

The devices described herein can be used to remove thromboembolic material from the vertebral artery or other cerebrovascular vessel. The occlusion site can be first localized with transcranial Doppler and angiogram. The catheter can be inserted through an incision on a peripheral artery into the symptomatic vertebral artery or the subclavian artery. For example, the distal end of a guide catheter can be inserted proximal to thromboembolic material in right vertebral artery and left subclavian artery. The foreign body removal catheter can be advanced through the thromboembolic material so that it resides distal thereto. The expandable region is expanded using fluidic systems to a second, larger diameter. The expandable catheter is withdrawn proximally, pulling the thromboembolic material therewith and into the open distal end of the guide catheter. The thromboembolic material may thereafter be removed from the vessel, optionally with the assistance of continuous or pulsed suction, thereby reducing the risk of embolization to the basilar artery.

Access for the catheter of the present invention can be achieved using conventional techniques through an incision on a peripheral artery, such as right femoral artery, left femoral artery, right radial artery, left radial artery, right brachial artery, left brachial artery, right axillary artery, left axillary artery, right subclavian artery, or left subclavian artery. An incision can also be made on right carotid artery or left carotid artery 130 in emergency situations.

The length of the catheter for those access sites to reach the brain will generally be between about 20 and 150 centimeters, preferably approximately between 60 and 130 centimeters. The inner diameter of the catheter may be between about 0.010 and 0.050 inches.

Figure 1A:
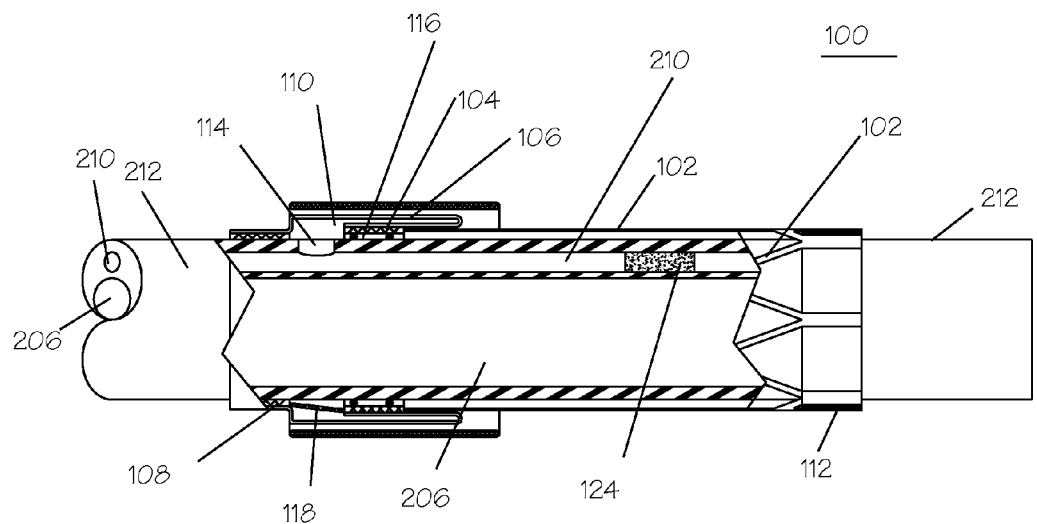
FIG. 1A illustrates a side view, in partial cross-section, of the distal end of a catheter, configured to be introduced through a guide catheter, comprising a radially expandable region near its distal end.

FIG. 1A illustrates the distal end 100 of the catheter whose proximal end 100 is illustrated in FIG. 1A. The distal end 100 comprises the catheter shaft 212, the central lumen 206 and the pressurization lumen 210. The distal end 100 further comprises an expandable mesh 102, an activation bladder 106, a pressure lumen plug 124, a proximal bladder to catheter tubing weld 108, and a distal bladder slider ring 104 separated from the catheter shaft 212 by a slider ring gap 116. The distal end 100 yet further comprises the pressurization port 114 and the inner volume 110 of the bladder 106. In the illustrated embodiment, the distal end 100 further comprises a return spring 118.

Referring to FIG. 1A, the distal bladder slider ring 104 is affixed to the distal end of the bladder 106. The distal bladder slider ring 104 is also affixed to the proximal end of the expandable mesh or structure 102. The ring 104 can be affixed to the bladder 106 by adhesives, heat welding, clamps, pins, or the like. The ring 104 can be heat welded, insert molded, mechanically attached, or otherwise affixed to the expandable structure 102. The return spring 118 can be affixed to the ring 104 by welding, adhesives, mechanical fixation devices such as pins, screws, clamps, or the like. The return spring 118 can be fabricated from elastomeric materials having resistance to permanent deformation. Such elastomeric materials include polyurethane, Hytrel, silicone, stainless steel, nitinol, and the like. Metal springs can be formed as coils, serpentine, or other bent structures. Polymeric elastomers can be formed into threads, rods, sheets, or the like and simply stretch under the influence of the pressurized forcing of the ring 104 distally. During shipping and storage, the spring will be unstressed and, thus not eventually fail due to creep or material elongation during a long-term period of stretching.

The purpose of the pressure lumen plug 124 is to prevent leakage of pressurized fluid from the distal end of the pressure lumen 210 during pressurization to advance the ring 104 distally. In other embodiments, the pressure lumen 210 can be melted closed using heat, solvents, pressure, or other energy. The plug 124 is beneficial since it would be difficult and expensive to have the plug built into (integral to) the extrusion of the catheter tube 212, although this alternative is certainly possible.

Figure 1B:
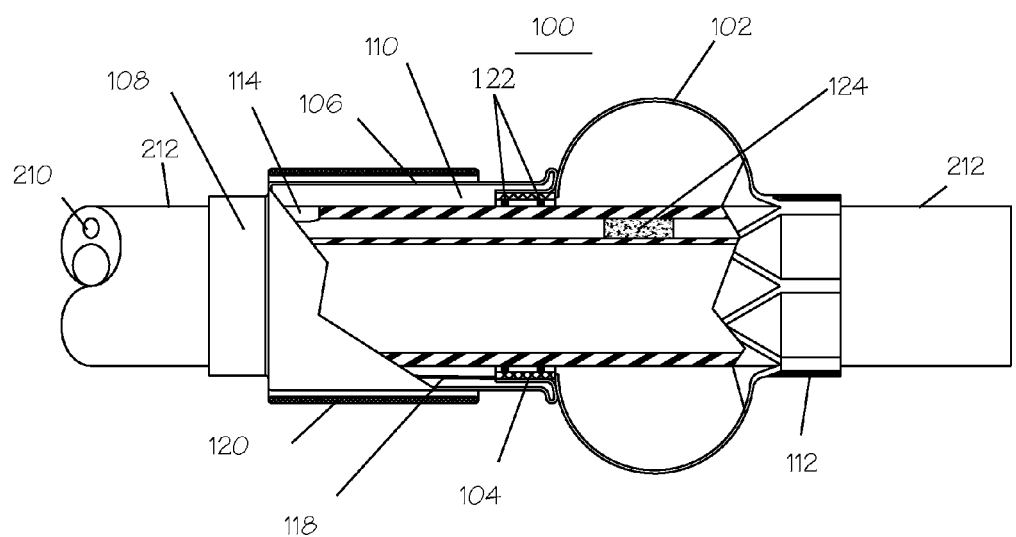
FIG. 1B illustrates a side view, in partial cross-section, of the distal end of the catheter of FIG. 1A wherein the proximal end of the expandable region has been advanced distally by introduction of fluid into a plunger system.

FIG. 1B illustrates the distal end 100 wherein interior volume 110 of the bladder 106 has been pressurized with incompressible fluid through the lumen 210 and the port 114. The distal end 100 comprises the catheter shaft 212, the central lumen 206, the pressurization lumen 210, and the pressure lumen plug 124. The distal end 100 further comprises the expandable mesh 102, the activation bladder 106, the proximal bladder to catheter tubing weld 108, and the distal bladder slider ring 104 separated from the catheter shaft 212 by the slider ring gap 116. The distal end 100 yet further comprises the pressurization port 114, the inner volume 110 of the bladder 106, and the return spring 118. The system can also comprise an optional external sleeve 120 to prevent excessive diametric expansion of the bladder or bag 106. Optionally, the inside of the slider ring 104 can comprise an affixed bushing, "O-rings", or gasket 122.

Referring to FIG. 1B, pressurization of the volume 110 has caused the bladder 106 to expand in the only direction possible, distally. The distal ring or sliding seal 104 moves distally and the material making up the bladder 106 is substantially inelastic so the bladder 106 cannot increase in diameter under the applied pressure. Instead, the distal end of the bladder 106, and its affixed ring 104, slides distally by way of the small gap 116 between the ring 104 and the catheter tube 212. The small gap 116 provides for low friction and is configured to seal against fluid loss from the internal volume 110. The ring 104 performs the function of a bushing or bearing with close tolerances to the catheter shaft 212. An optional, leak-proof gasket or bushing 122 can be disposed in the space 116 (see FIG. 1A), affixed to the interior of the ring 104, to prevent fluid or pressure leakage from the internal region 110 of the bag 106.

Figure 2:
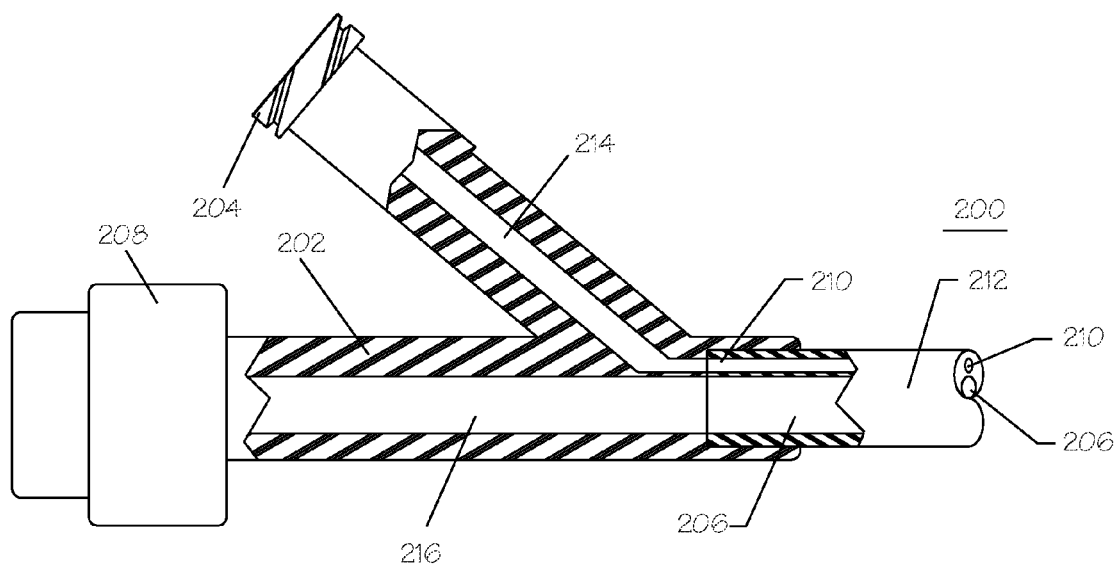
FIG. 2 illustrates a side view, in partial cross-section, of the proximal end of a catheter, configured to be introduced through a guide catheter, comprising a central lumen and an inflation lumen.

FIG. 2 illustrates the proximal end 200, in partial breakaway cross-section, of a catheter configured to expand at its distal end, the proximal end 200 comprising a hub 202, further comprising a Luer sideport 204, a through lumen 216, a hemostasis valve 208, and a side pressurization lumen 214. The proximal end 200 further comprises a catheter shaft or length of catheter tubing 212 further comprising a through lumen 206 and a pressurization lumen 210.

Referring to FIG. 2, the catheter 212 is affixed to the hub 202 by adhesives, welding, insert molding, or the like. The pressurization lumen 214 of the hub 202 is operably connected to the pressurization lumen 210 inside the catheter tubing 212. The Luer port 204 is operably connected to the pressurization lumen 214, which is operably connected to the catheter pressurization lumen 210. The hemostasis valve 208 is affixed to the proximal end of the hub 202. The hemostasis valve 208 comprises a central lumen (not shown), which is operably connected to the central lumen 216 of the hub 202. The central hub lumen 216 is operably connected to the through lumen 206 of the catheter.

Figure 3A:
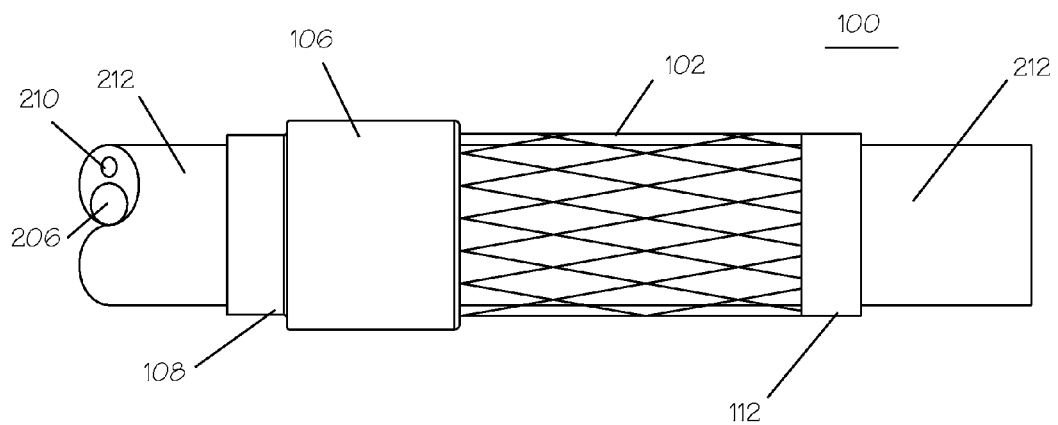
FIG. 3A illustrates a side exterior view of the distal end of a therapeutic catheter in its radially collapsed state.

FIG. 3A illustrates an exterior view of the distal end 100 of the catheter comprising the catheter tube 212 further comprising the pressure lumen 210 and the through lumen 206. The distal end 100 further comprises the bag 106, the proximal bag to catheter weld 108, the expandable structure 102, and the distal expandable structure to catheter weld 112.

Referring to FIG. 3A, the ring (not shown) is retracted proximally under the bag 106 and so is not visible. The optional external restraint or sleeve 120 of FIG. 1B is not present in this embodiment. The elements of the expandable structure 102, which in this embodiment is a mesh, are stretched out longitudinally to nearly parallel the axis of the catheter shaft 212.

Figure 3B:
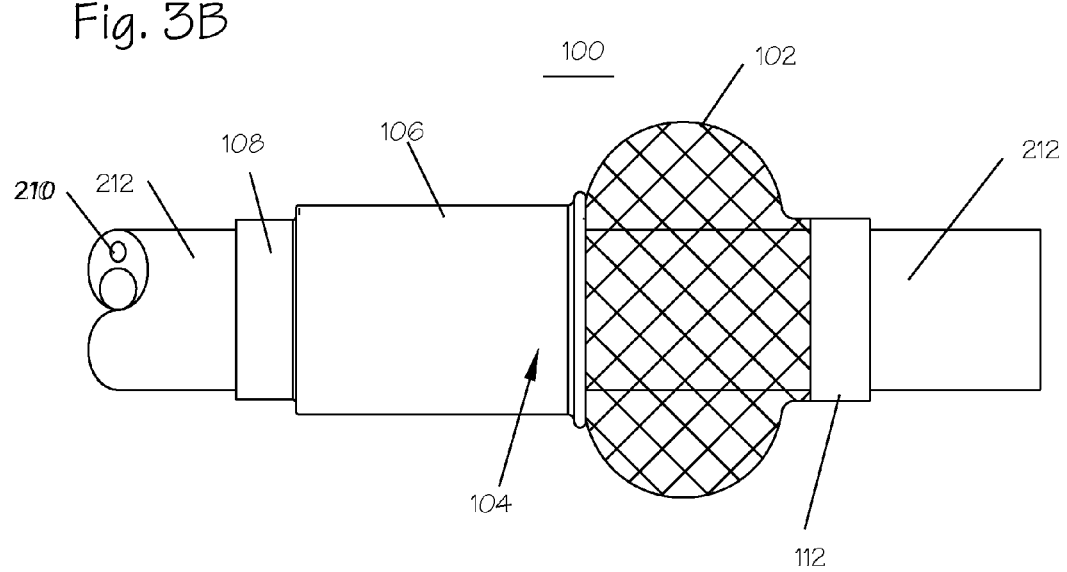
FIG. 3B illustrates a side exterior view of the distal end of the therapeutic catheter of FIG. 3A in its radially expanded state.

FIG. 3B illustrates an exterior view of the distal end 100 of the catheter comprising the catheter tube 212 further comprising the pressure lumen 210 and the through lumen 206. The distal end 100 further comprises the bag 106, the proximal bag to catheter weld 108, the expandable structure 102, and the distal expandable structure to catheter weld 112.

Referring to FIG. 3B, the bag 106 has been inflated and its distal end has uneverted and moved distally to force the proximal end of the mesh 102 distally. The mesh 102 has become an expanded annular structure with a greater diameter or lateral dimension than in its unexpanded state of FIG. 3A. The fold or eversion at the distal end of the bag 106 is visible up against the proximal end of the mesh 102. The ring 104 can move a distance of about 1 mm to about 20 mm and, in a preferred embodiment the ring 104 can move about 2 mm to about 10 mm, and in a more preferred embodiment the ring 104 can move about 3 mm to about 6 mm.

The expandable structure 102 can take the form of a mesh, or a series of fingers, battens, rods, or a malecot, longitudinally disposed along the exterior of the catheter shaft 212 but disconnected from the catheter shaft 212 except at the distal bond 112 and at the slidably movable ring 104 hidden under the bag 204. The mesh can be fabricated from polymeric materials such as PET, Nylon, PEEK, silicone, or the like, or it can be fabricated from metals such as nitinol, stainless steel, tantalum, platinum, cobalt nickel alloy, and the like.

The catheter shaft can range from about 1 French to about 7 French in outside diameter with a preferred range of about 2 French to about 5 French in outside diameter. The expandable structure 102, when fully expanded, can range in outside diameter from about 3 French to about 15 French, depending on the diameter of the catheter shaft.

FIG. 4A illustrates a side view, in partial breakaway of the distal end 450 of a therapeutic catheter 400. The distal end 450 comprises a guidewire 402, an inner catheter tube 410 further comprising an inner catheter tube lumen 412, an outer catheter tube 414 further comprising an outer catheter tube lumen 416, an annular piston 404, a pusher 406, an elastomeric sleeve 408, a proximal expandable member bearing 428, a proximal bearing attachment 429, an expandable member 426, a fluid impermeable layer 430, one or more expandable member radiopaque markers 418, an expandable member distal end 420, a distal expandable member bond 424, and a distal radiopaque tube marker 422. In this illustration, the catheter distal end 450 is typically deployed within the cardiovascular system such that the natural blood flow moves from the proximal end toward the distal end, but the reverse direction is also possible.

Referring to FIG. 4A, the inner tube 410 is disposed generally concentrically within the lumen 416 of the outer tube 414 and is constrained not to slide longitudinally relative to the outer tube 414. The distal end 420 of the expandable structure 426 is affixed at its distal end to the inner tube 410 by the distal bond 424. The distal end 420 of the expandable structure 426 can be affixed to the inner tube 410 near the distal end of the inner tube 410 but could also be affixed substantially proximal to that location resulting in substantial projection of the inner tube 410 beyond the distal end 420 of the expandable structure 426. The expandable member 426 can comprise any structure including mesh, weave, braid, longitudinally oriented bars or struts, or the like. In a preferred embodiment, the expandable member 426 comprises a braid of stainless steel, cobalt nickel alloy, nitinol, or other high-spring, biocompatible metal wires having spring temper and having individual strand diameters of about 0.001 inches. The pick count of the braid can be between 5 and 100 picks per inch and the number of ends can range between about 6 to about 64. The length of the expandable member 426 can range from about 1-mm to about 300-mm and the outer diameter of the expandable member can range from about 1 mm to about 40 mm, depending on the target vessel and its therapeutic or diagnostic purpose, when in the fully expanded configuration. The inner catheter shaft or tube 410 can range from about 1-French to about 10-French in outside diameter with a preferred range of about 2-French to about 5-French in outside diameter. The guidewire 402 is slidably disposed within the lumen 412 of the inner tube 410 and is used to track the catheter 400 or maintain position within a lumen.

The distal end of the annular piston 404 is affixed to the proximal end of the pusher 406 by welding, mechanical attachment, bonding, or the like. The annular piston 404 is sized to fit between the inner diameter of the outer tube 414 and the outer diameter of the inner tube 410. The piston 404 rides within the inner lumen 416 of the outer tube 414 but its travel space is reduced by the presence of the inner tube 410 thus resulting in an annulus-shaped inner lumen 416. The annular piston 404 can slide along the longitudinal axis of the tubes but maintains a fluid-tight gap between the two tubes.

The pusher 406 can be fabricated as a cylinder, one or more rods, a cone, a coiled cylinder with no gaps between the coils, a conical coil with no gaps between the coils, or similar structure. The coil configuration permits flexibility along the region of the pusher while maintaining column strength. The pusher 406 is affixed, at its distal end, to the proximal end bearing 428 of the expandable member 426, or to the proximal end of the expandable member 426, itself, by the proximal bearing attachment or bond 429. The proximal end bearing 428 of the expandable member 426 can have its inner surface lined with lubricious materials such as, but not limited to, PTFE, silicone oil, PFA, FEP, or the like so that it slides with minimal interference or restraint over the outside diameter of the inner tube 410. The pusher 406 preferably has in inside diameter that clears the inner tube 410 so that friction is very low or non-existent in this region. The proximal end bearing 428 is affixed to the proximal end of the expandable member 426.

The elastomeric sleeve 408 serves as a return spring for the proximal end of the expandable member 426. The elastomeric sleeve is affixed to the distal end of the outer tube 414 at its proximal end and to the proximal end of the expandable member, the distal end of the pusher, or to the proximal end bearing 428. The elastomeric sleeve 408 can be configured as a polymeric cylinder or conical cylinder. In other embodiments, the elastomeric sleeve 408 can be configured such that it is not a sleeve but a linear, coiled, bent, or serpentine spring. The elastomeric sleeve 408 can be fabricated from materials such as, but not limited to, polyurethane, Chronoprene™, stainless steel, nitinol, cobalt nickel alloy, titanium, silicone elastomer, or the like.

The fluid impermeable layer 430 is optional and is configured to line the inside, the outside, or both of the expandable member 426. The fluid impermeable layer 430 can be disposed over the entirety or a portion of the expandable member 426. The fluid impermeable layer 430 can comprise a thin membrane. The fluid impermeable layer can comprise a polymeric material.

FIG. 4B Illustrates a side, partial breakaway, view of the distal end 450 of the catheter 400 of FIG. 4A in its second, radially expanded configuration. The distal end 450 comprises the guidewire 402, the inner catheter tube 410 further comprising the inner catheter tube lumen 412, the outer catheter tube 414 further comprising the outer catheter tube lumen 416, the annular piston 404, the pusher 406, the elastomeric sleeve 408, the proximal expandable member bearing 428, the proximal bearing attachment 429, the expandable member 426, the fluid impermeable layer 430, the expandable member radiopaque markers 418, the expandable member distal end 420, the distal expandable member bond 424, and the distal radiopaque tube marker 422.

The annulus-shaped lumen 416 is pressurized with fluid, preferably liquid, and has forced the annular piston 404 toward the distal end of the outer tube 414. The annular piston 404 has moved closer to the distal end of the outer tube 414 forcing the pusher 406 to move distally over the stationary inner tube 410.

The pusher forces the proximal end of the expandable region 426 to move distally to reduce the distance between the proximal end and bearing 428 relative to the stationary distal end 420 of the expandable region 426. The axial length reduction of the expandable region 426 as generated a laterally directed outward displacement of the center of the expandable region 426.

The elastomeric sleeve 408 has stretched and is generating a restorative bias force to pull the proximal end of the expandable region 426 back to its unexpanded condition. The length of the pusher 406 is configured to permit optimal performance of the elastomeric sleeve 408, the spring function of which is improved by having a substantial length over which to operate such that the structure is not strained beyond its elastic limit.

Figure 5:
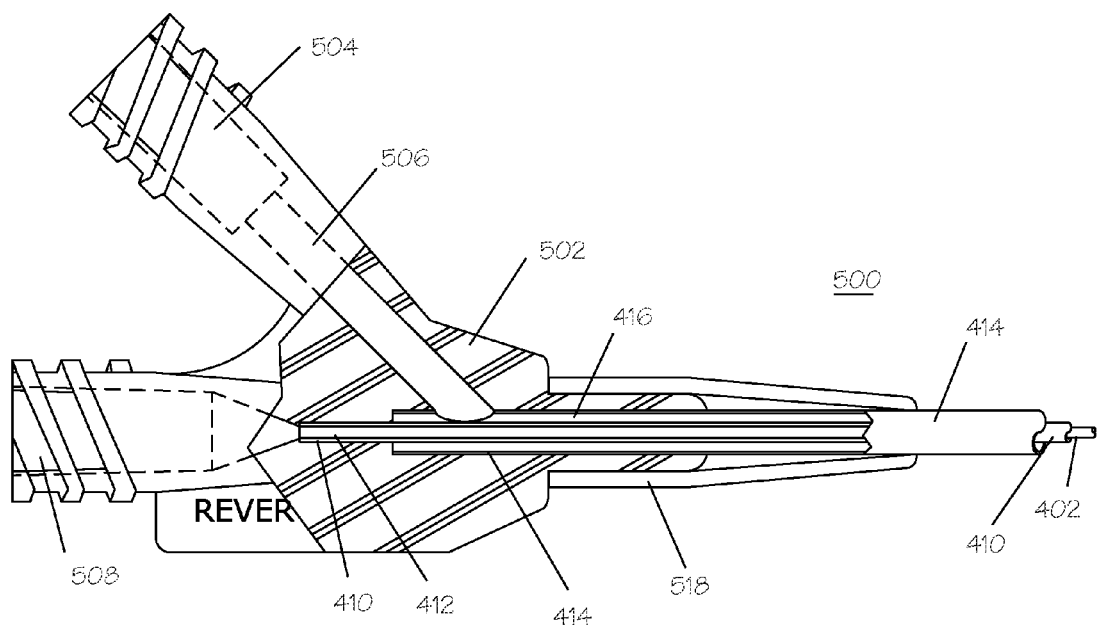
FIG. 5 illustrates a side partial breakaway view of the proximal end of the therapeutic catheter of FIGS. 4A and 4B, according to an embodiment of the invention.

FIG. 5 illustrates the proximal end 500 of the catheter 400 in a side, partial breakaway view. The proximal end 500 comprises a hub 502 further comprising a central lumen access port 508, a side lumen access port 504, and a side lumen manifold lumen 506. The proximal end 500 further comprises the guidewire 402, the inner catheter tube 410 further comprising the inner catheter tube lumen 412, the outer catheter tube 414 further comprising the outer catheter tube lumen 416, and the strain relief 518.

Referring to FIG. 5, the hub 502 is bonded, welded, overmolded, or otherwise affixed to the inner tube 410 and the outer tube 414 such that the inner lumen 412 of the inner tube 410 is operably connected to the through inlet port 508. The inner lumen 416 of the outer tube 414 is operably connected to the side manifold lumen 506 which is operably connected to the side inlet port 504. The inner lumen 416 forms an annulus with the outside diameter of the inner tube 410. Access to the inner lumen 416 can be obtained through a port, as illustrated, or through the proximal end of the outer tube 414, in other embodiments. In the illustrated embodiment, the proximal end of the inner lumen 416 is sealed against fluid leakage so that the manifold lumen 506 provides the only access to the inner lumen 416 at the proximal end 500 of the catheter 400. The side inlet port 504 and the through inlet port 508 are preferably configured with Luer type fittings but can be configured with other bayonet, screw, clamp, press-fit, or quick connect features. The proximal end of the strain relief 518 is affixed to the hub 502 and the distal end is coaxially disposed over the outer tube 414. The distal end of the strain relief 518 can be affixed to the outer tube 414 or be longitudinally free to move.

The through inlet port 508 generally accepts the guidewire 402 and is preferably affixed, and operably connect, to a hemostasis valve (not shown). The side inlet port 504 is configured for high pressure injection of fluid, preferably liquids such as, but not limited to, water, saline, radiopaque dye contrast media, or a combination thereof. Fluid injected into the side inlet port 504 flows through the manifold lumen 506 into the annulus 416 within the outer tube 414 such that it pressurizes the lumen annulus 416 and moves the annular piston 404 of FIGS. 4A and 4B. Withdrawal of vacuum on the side inlet port 504 can be used to generate a corresponding proximal motion of the annular piston 404 to augment or completely generate proximal movement of the proximal end of the expandable member 426 of FIGS. 4A and 4B.

The catheter is inserted into the patient through an already placed guide catheter or over an already placed guidewire. The catheter can be inserted using a cutdown or using percutaneous technique. The percutaneous technique can include techniques such as the Seldinger technique in which a hollow needle is introduced into the vessel through the skin followed by guidewire insertion and removal of the hollow needle to permit a catheter to be placed over the guidewire, or similar types of methodology. The catheter, in other embodiments, can be inserted simultaneously with the guidewire such that maneuvering and steering is accomplished with a bent end of the guidewire or the expandable catheter. Once advanced to the desired location, the expandable catheter position is confirmed under fluoroscopy, ultrasound, MRI or other imaging modality.

Fluid can be injected, under pressure, into the inflation port on the proximal hub of the catheter. The fluid pressurizes a region inside a bladder or bag causing axial movement of a ring attached to the proximal or distal end of an expandable region. The bladder or bag is restricted from radial expansion due to inelastic properties, inelastic reinforcing materials, or a restraining sleeve or mesh such as a weave, braid, knit or other structure. One end of the bag or bladder is affixed to the catheter shaft but the other end of the bladder or bag is affixed to the ring and forces the ring to move along the axis of the catheter shaft, slidably movable thereupon. The fluid is injected by the operator using a syringe or a commercial inflation device comprising a syringe and a threaded jack screw or ratcheting mechanism. A small syringe, such as one with a ¼ cc volume can generate more than 1000 PSI under thumb pressure. Larger syringes can generate less pressure but provide higher fluid volumes. The volume required will be small and is a function of the annulus between the catheter shaft and the bag or the annulus between the inner tube 410 and outer tube 414.

By infusing fluid into the pressurization channel and the volume under the bag, the ring can be moved and the expandable region expanded diametrically. The catheter can be used for a variety of therapeutic or diagnostic purposes including, but not limited to, embolic material introduction, implant (e.g. stent) deployment, temporary flow restoration, thrombolytic material introduction, neck bridging, aneurysm embolization, embolization of arteriovenous malformations (AVM), embolic protection filter deployment, radiopaque contrast injection, and MRA fluid injection.

Upon completion of the therapy or diagnostics, fluid is removed from the pressure port and pressure lumen. Upon removal of the fluid, the expandable region can return to its initial, unexpanded state under its own resilience. The expandable region can be fabricated from elastomeric or spring materials to facilitate this restoration movement. The restoration to unexpanded state can be enhanced by the addition of a spring between the ring and the proximal bond between the bag and catheter shaft, or other suitable location. The catheter can now be moved to a new location or removed from the body vessel or lumen. The guidewire, guide catheter, or both can be left in place following removal of the catheter with the expandable element.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. A thrombus removal system comprising:
    an axially elongate catheter tube having a proximal end, a distal end, and comprising a central lumen and a pressurization lumen extending from the proximal end toward the distal end;
    a fluid infusion port at the proximal end operably connected to the pressurization lumen of the catheter tube;
    a through port operably connected to the central lumen of the catheter tube;
    an expandable structure proximate the distal end of the catheter tube capable of enlarging or reducing in lateral dimension in response to axially longitudinal movement of a proximal end of the expandable structure relative to a distal end of the expandable structure, the proximal end of the expandable structure slidable along the catheter tube while having a constant diameter whether the expandable structure is enlarged or reduced in size, and the distal end of the expandable structure being fixed relative to the catheter tube;
    a bladder affixed at one end to the proximal end of the expandable structure and at another end to the catheter tube, wherein an inner volume of the bladder exists between the bladder and the catheter tube; and
    a pressurization port operably connecting the pressurization lumen with the inner volume between the bladder and the catheter tube.

2. The system of claim 1, further comprising a return spring coupled to the proximal end of the expandable structure and capable of moving the proximal end of the expandable structure from a second position to a first position.

3. The system of claim 1, further comprising a sliding seal coupled to the proximal end of the expandable structure to restrict loss of fluid pressure while permitting longitudinal movement of the proximal end of the expandable structure.

4. The system of claim 1, wherein the expandable structure comprises a mesh coupled to ring structures at the proximal end of the expandable structure and the distal end of the expandable structure.

5. The system of claim 1, wherein the expandable structure comprises a plurality of longitudinal struts that are connected to ring structures at the proximal end of the expandable structure and the distal end of the expandable structure.

6. The system of claim 1, further comprising a pressurized source of fluid configured to be removably coupled to the proximal end of the catheter tube via the infusion port.

7. The system of claim 1, wherein the expandable structure is covered, at least in part, with a thin membrane fabricated from polymeric materials.

8. The system of claim 1, wherein distal movement of the proximal end of the expandable structure causes a central region of the expandable structure to enlarge in a direction lateral to an axis of the catheter tube.

9. The system of claim 1, wherein proximal movement of the proximal end of the expandable structure causes a central region of the expandable structure to decrease in lateral dimension.

10. A method of delivering therapy to the vasculature of a patient comprising: percutaneously introducing a guidewire into an artery of a patient;
   advancing a guide catheter over the guidewire to a region proximate a target region within the vasculature;
   removing the guidewire;
   introducing a therapeutic catheter through the guide catheter, the therapeutic catheter comprising an axially elongate catheter tube having proximal and distal ends, a central lumen, and a pressurization lumen extending from the proximal end toward the distal end; the therapeutic catheter further comprising a fluid infusion port, a through port, an expandable structure, and a bladder; the fluid infusion port proximate the proximal end and operably connected to the pressurization lumen; the through port operably connected to the central lumen; the expandable structure proximate the distal end and capable of enlarging or reducing in lateral dimension in response to axially longitudinal movement of a proximal end of the expandable structure relative to a distal end of the expandable structure; the bladder being affixed at one end to the proximal end of the expandable structure and at another end to the catheter tube, wherein an inner volume of the bladder exists between the bladder and the catheter tube;
   advancing the therapeutic catheter out the distal end of the guide catheter to engage the target region;
   moving the therapeutic catheter at least partially through the target region;
   introducing fluid, under pressure, to the fluid infusion port, said fluid moving through the pressurization lumen and a pressurization port, the pressurization port operably connecting the pressurization lumen with the inner volume of the bladder, said fluid pressurizing the inner volume;
   moving the proximal end of the expandable structure under force by the pressurized fluid beneath the bladder and the catheter tube, the proximal end of the expandable structure slidable along the catheter tube while having a constant diameter whether the expandable structure is enlarged or reduced in size, and the distal end of the expandable structure being fixed relative to the catheter tube;
   expanding a central portion of the expandable structure in a lateral dimension;
   performing a therapeutic action while the central portion of the expandable structure is expanded; and
   reducing the expandable structure in lateral dimension by removal of fluid pressure at the proximal end of the therapeutic catheter.

11. The method of claim 10 further comprising the step of removing the therapeutic catheter from the vasculature of the patient.

12. The method of claim 10 further comprising the step of withdrawing the expanded expandable structure proximally to engage the distal end of the guide catheter.

13. The method of claim 10 further comprising the step of assisting in reducing the expandable structure in lateral dimension by resilient recoil of a spring affixed to the proximal end of the expandable structure.

14. The method of claim 10 wherein the therapeutic catheter is used to perform thrombectomy.

15. The method of claim 10 wherein the therapeutic catheter is used to provide a filter or net to prevent passage of a thrombus or foreign body while permitting passage of blood therethrough.

16. The method of claim 10 wherein the therapeutic catheter is used to deliver thrombolytic material to the vasculature.

17. The method of claim 10 wherein the therapeutic catheter is used to form a temporary opening in a substantially stenosed vessel.

18. The method of claim 10 wherein the therapeutic catheter is used to provide a temporary neck bridge to an aneurysm.

19. The method of claim 10 wherein the therapeutic catheter is used to delivery embolic material to the vasculature.

20. The method of claim 10 wherein the target region is within cerebrovasculature.

* * * * *